United States Patent [19]

Evans et al.

[11] Patent Number: 4,977,290

[45] Date of Patent: Dec. 11, 1990

[54] POLAR APROTIC CATALYSTS FOR FORMATION OF FLUOROSILICONE FLUIDS

[75] Inventors: Edwin R. Evans; Paul Maitoza, both of Clifton Park, N.Y.

[73] Assignee: General Electric Company, Waterford, N.Y.

[21] Appl. No.: 439,968

[22] Filed: Nov. 20, 1989

[51] Int. Cl.$^5$ .................................................. C07F 7/08
[52] U.S. Cl. ..................................................... 556/459
[58] Field of Search ......................................... 356/459

[56] References Cited

U.S. PATENT DOCUMENTS

| | | | |
|---|---|---|---|
| 2,634,284 | 4/1953 | Hyde | 260/448.2 |
| 2,863,897 | 12/1958 | Wehrly | 556/459 |
| 3,268,570 | 8/1966 | Weyenberg | 556/459 X |
| 3,853,932 | 12/1974 | Razzano | 260/448.2 |
| 4,282,353 | 9/1981 | Bluestein | 556/459 |
| 4,317,899 | 3/1982 | Bluestein | 556/467 |

*Primary Examiner*—Paul F. Shaver

[57] ABSTRACT

There is provided a process for producing low molecular weight silanol end-stopped diorganopolysiloxanes containing an average of 3 to 10 diorganosiloxy units and averaging 5 diorganosiloxy units comprising contacting a cyclic trimer of the formula:

$$(R^2SiO)_3$$

where $R^2$ is a halogenated monovalent hydrocarbon radical and R is selected from the class consisting of monovalent hydrocarbon radicals and halogenated monovalent hydrocarbon radicals with a mixture comprising an aprotic solvent and water and separating the desired product after the hydrolysis.

6 Claims, No Drawings

POLAR APROTIC CATALYSTS FOR FORMATION OF FLUOROSILICONE FLUIDS

CROSS REFERENCE TO RELATED APPLICATIONS

Reference is made to the concurrently filed application identified as U.S. Ser. No. 07/439,741, filed Nov. 20, 1989.

BACKGROUND OF THE INVENTION

The present invention relates to the production of low molecular weight silanol end-stopped diorganopolysiloxanes and more particularly the present invention relates to the production of low molecular weight silanol end-stopped diorganopolysiloxanes from cyclic trisiloxanes with the use of an aprotic solvent acting as a catalyst.

Low molecular weight silanol-stopped diorganopolysiloxanes having an average number of anywhere from three to 10 diorganosiloxy units have many uses including as intermediates for the production of high molecular weight polymers, as additives for the preparation of heat vulcanizable silicone rubber compositions and room temperature vulcanizable silicone rubber compositions and also as additives for the preparation of organic rubbers. In particular, such low molecular weight silanol-stopped diorganopolysiloxanes have found wide use as process aids. Such process aids are utilized as additives to both fumed silica and precipitated silica fillers that are added to mix with diorganopolysiloxane gums in the preparation of heat vulcanizable silicone rubber compositions. Such silanol-stopped materials are added with the filler and gum as the filler is incorporated or mixed into the high molecular weight diorganopolysiloxane gum so as to facilitate the intermixing of the filler and the gum.

The silanol end-stopped diorganopolysiloxanes also improve the final properties of the heat vulcanizable silicone rubber composition in both the cured and uncured state. In the cured state the silanol end-stopped diorganopolysiloxanes impart elasticity. In the uncured state the silanol endstopped diorganopolysiloxanes prevent excessive hardening upon storage.

Another important use of the low molecular weight silanol-stopped diorganopolysiloxanes of the present case is that they may be used as intermediates and condensed so as to form high molecular weight polymers, such as fluorosilicone polymers of high molecular weight, in a manner in which the final viscosity of the polymer is precisely controlled. These fluorosilicone-containing polymers can be, of course, utilized to prepare solvent resistant, fluorosilicone elastomers.

In the past, one method for producing such silanol-stopped diorganopolysiloxanes of low molecular weight was to take diorganodichlorosilanes of 99 percent purity or so and hydrolyze them in water in the presence of large amounts of polar solvent. While such diorganodichlorosilanes were added to the water polar solvent mixture there was continuously present, or added at the time of addition of the diorganodichlorosilanes, large amounts of sodium bicarbonate so as to maintain the neutrality of the hydrolysis solution. Both the sodium bicarbonate and the excess amounts of polar solvent were necessary in order to prepare the low molecular weight silanol-stopped diorganopolysiloxanes. If enough polar solvent was not utilized or if enough sodium bicarbonate was not added the silanol groups of the resultant silanol-stopped diorganopolysiloxanes would condense with each other forming high molecular weight silanol-stopped diorganopolysiloxanes which are not considered to be particularly desirable.

This process outlined above is undesirable for various reasons, one of which is the large amount of buffering agents that have to be added to the hydrolysis mixture, thus necessitating very large equipment space. In addition, the salted water phase that is formed after the hydrolysis reaction has to be purified before it can be disposed of. Further, the yield was is lower than expected since the water layer, after the hydrolysis reaction, has to be separated from the polar solvent layer. During this separation step some of the desired end product is lost in the water layer. Accordingly, as one purpose of this invention, it is desired to improve on this process.

One means accomplishing this purpose is disclosed in Omietanski, U.S. Pat. No. 3,309,390. Omietanski discloses the production of low molecular weight silanol-stopped diorganopolysiloxanes from cyclic trisiloxanes through the use of an ion exchange resin. A disadvantage with the Omietanski process is that it uses an ion exchange resin. Such ion exchange resins are unduly expensive. As such they cannot be thrown away after they have spent themselves, and time and effort must be made to regenerate them. The additional time and chemicals necessary to regenerate the ion exchange resin, of course, adds to the expense of the process. In addition, such ion exchange resins may have a certain amount of residual acidity on the resin which has to be washed off before it can be utilized in the Omietanski process. Otherwise, the low molecular weight silanol-stopped diorganopolysiloxanes that are formed from the process may contain an excessive amount of acidity which will result in the condensation of the silanol groups of the desired product.

It has also been found that acid-activated carbon black will not operate in such a process. When used, the desired low molecular weight diorganopolysiloxanes are not obtained.

Another means for accomplishing the purposes of this invention is taught by Razzano in U.S. Pat. No. 3,853,932. Therein, cyclic triorganopolysiloxanes are catalyzed by acidactivated hydroaluminum silicate clay in the presence of water and a polar organic solvent. This process, however, suffers from the some of the same problems stated above. Namely, the ring-opening hydrolysis is a multi-step process that requires a number of pieces of equipment. Further, the acid activated clay must be separated from the resultant product in order to avoid stability problems. This separation process is costly, requires additional equipment, and results in product loss and decreased efficiency.

Accordingly, it is one object of the present invention to provide an inexpensive and efficient catalyst for the production of low molecular weight silanol-stopped diorganopolysiloxanes from cyclic trisiloxanes.

It is an additional object of the present invention to provide a process for producing low molecular weight silanolstopped diorganopolysiloxanes from cyclic trisiloxanes so as to obtain such low molecular weight silanol-stopped diorganopolysiloxanes in high yield.

It is an additional object of the present invention to provide a process for producing low molecular weight silanolstopped diorganopolysiloxanes which can be used as intermediates to produce high molecular weight fluorosilicon polymers.

These and other objects of the present invention are accomplished by means of the disclosure set forth below.

SUMMARY OF THE INVENTION

According to the objectives of the invention there is provided a process for producing low molecular weight silanol end-stopped diorganopolysiloxanes containing an average of 3 to 10 diorganosiloxy units and averaging 6 diorganosiloxy units comprising contacting a cyclic trimer of the formula:

$(R^2RSiO)_3$ where R is selected from the class consisting of monovalent hydrocarbon radicals and halogenated monovalent hydrocarbon radicals and $R^2$ is a halogenated monovalent hydrocarbon radical with a mixture comprising an aprotic solvent and water and separating the desired product after the hydrolysis.

DETAILED DESCRIPTION OF THE INVENTION

By this invention there is provided a process for producing low molecular weight silanol end-stopped diorganopolysiloxanes containing an average of 3 to 10 diorganosiloxy units and averaging 6 diorganosiloxy units comprising contacting a cyclic trimer of the formula:

$(R_2SiO)_3$ where a is selected from the class consisting of monovalent hydrocarbon radicals and halogenated monovalent hydrocarbon radicals, and $R^2$ is a halogenated monovalent hydrocarbon radical with a mixture comprising an aprotic solvent and water and separating the desired product after the hydrolysis.

Preferably, each R radical in the cyclic trimer is selected from the alkyl radicals of one to eight carbon atoms, haloalkyl radicals of one to eight carbon atoms, and cycloalkyl radicals of one to eight carbon atoms. Such radicals include, but are not limited to, methyl, ethyl, propyl, butyl, monochloromethyl, monochloroethyl, monochloropropyl, monofluoromethyl, difluoroethyl, trifluoropropyl, and cycloheptyl.

Preferably, each R radical is selected from alkyl radicals of one to eight carbon atoms and a monovalent group represented by the formula:

$R^1CH_2CH_2-$ where $R^1$ is a perfluoroalkyl radical. Most preferably, each R radical is selected from the group consisting of methyl and trifluoropropyl.

To obtain the starting cyclic trimer for use in the process of the present invention, there is first taken a diorganodihalogensilane of the formula $R_2SiX_2$, where R is as previously defined and X is a halogen, preferably chlorine. The diorganohalogensilane is added to water at approximately room temperature. It is preferable that the silane is added to the water slowly so as to maintain the water hydrolysis temperature at room temperature or below. This is to inhibit the escape of boiling silanes from the hydrolysis mixture. If the reaction temperature rises above room temperature, it is necessary for the reaction vessel to be equipped with condensors in order to return the silanes to the vessel.

In such a hydrolysis there will be formed in addition to the diols a certain amount of cyclic siloxanes which will comprise a mixture of cyclic trisiloxanes, cyclic tetrasiloxanes, cyclic pentasiloxanes, etc., all the way up to cyclic siloxanes that have 10 siloxy groups in the cyclic ring.

To purify and maximize the yield of cyclic trisiloxanes, it is traditional to separate the siloxy hydrolyzate mixture that is formed above from the water. To the siloxy hydrolyzate mixture is added an organic, water immiscible solvent such as a high boiling hydrocarbon oil so as to dissolve the siloxy hydrolyzate in the solvent. This solution of hydrolyzate in hydrocarbon is then heated for a period of one to five hours at reduced pressures. It may also be preferable to add an alkali metal catalyst such as sodium hydroxide or potassium hydroxide.

By preferentially distilling overhead cyclic trisiloxanes it is possible to obtain an yield of 96% based on the total siloxy hydrolyzate mixture and at a purity of 99%. This process for producing the halogenated trimer of this invention is set forth by Razzano in U.S. Pat. No. 3,853,932, herein incorporated by reference.

The aprotic solvents useful in this invention are polar solvents which neither donate nor accept protons. It has been found that such solvents will catalyze the ring-opening hydrolysis of halogenated cyclic trimers. Examples of these solvents include, but are not limited to, acetonitrile, dimethylacetimide, dimethylformamide, dimethylsulfoxide, n-methylpyrolidone, and propylene carbonate. Such solvents are readily obtainable from commercial sources. Of these listed, acetonitrile has been found to be preferable in that the resultant reaction proceeds more readily.

These aprotic solvents appear to lower the activation energy associated with the opening of the highly strained ring of the halogenated trimer. It is interesting to note, however, that the reaction with aprotic solvents is specific in that it preferentially opens the halogenated trimer and does not affect nonhalogenated cyclic siloxanes, even after protracted heating. This is probably the result of two things. Firstly, the halogenated trimers are highly strained rings which are affected by the polar nature of the aprotic solvent. Secondly, the aprotic solvents listed above appear to form ion-pair type complexes with water through hydrogen bonds. Thus, as the trimer ring is broken by the aprotic solvent, water is readily available to be inserted on the chain ends.

This theory helps to explain why acetonitrile, of all the aprotic solvents, appears to work best. Since acetonitrile hydrogen bonds with water more readily, the ring opening reaction is facilitated. This theory also helps to explain why acetone, which has a polarity index similar to that of acetonitrile, does not catalyze this reaction. Since acetone does not form the ion-pair type complex with water, insertion of the water onto the chain ends is hindered and the reaction does not proceed.

The amount of aprotic solvent necessary to effect the ring-opening hydrolysis is at least 50 ppm. Thus, the aprotic solvent may be contained in a mixture of solvents, and it will catalyze the ring-opening hydrolysis as long as the 50 ppm level is maintained. As an example of such a solvent mixture, the examples which follow demonstrate the use of acetonitrile in acetone. Although it is possible to use a solvent that consists entirely of an aprotic solvent, such solvents usually cost many times more than other commonly used solvents. By using a mixture, therefore, it is possible to economize the process without affecting the reaction.

It is also possible to use a mixture of one or more aprotic solvents or a mixture of one or more aprotic solvents and one or more nonaprotic solvents. The important point to remember is that there must be at least 50 ppm of aprotic solvent present to catalyze the reaction.

The amount of aprotic solvent necessary to practice this invention is also dependent on the temperature at which the reaction occurs. At 50 ppm the reaction usually occurs at about 80° C. If the level is increased to 150 ppm the reaction will occur at room temperature. From this it is also readily apparent that, no matter what the level of aprotic solvent, heating will facilitate the reaction.

When using a mixture of aprotic solvent(s) and nonaprotic solvent(s) it is necessary only that the different solvents be miscible with each other. In the combination mentioned above, acetonitrile in acetone, acetone was selected because it has a polarity that is similar to acetonitrile. This similarity in polarity allows for better homogeneity in the mixture.

Water, in this invention, acts to hydrolyze the trisiloxane chain ends upon ring opening of the halogenated trimer, thus forming a siloxane of about three siloxane units. The silanol chain ends may then further act as reactive sites for a condensation reaction mechanism.

For the best results there should be utilized an amount of water in excess of the stoichiometric amount. It is theorized that the water complexes with the aprotic solvent, and, as the aprotic solvent causes the trimer ring to break, these water molecules are then inserted onto the chain ends.

It is also important to note that water is the only useful hydrolyzing component. Neither silanols, e.g. Me₃SiOH, nor alcohols, e.g. Me₃COH, will act to hydrolyze the chain ends of the trimer as the ring is broken.

Another interesting feature of this reaction is the fact that silanols with a degree of polymerization averaging about 6 are produced. As a trimer is hydrolyzed it also undergoes a condensation reaction with adjacent silanols. This condensation reaction occurs almost immediately after the trimer is hydrolyzed, and it has been found very difficult to prevent from occurring. Thus, the degree of polymerization, after the reaction is complete, ranges from about 3 to about 10 with an average value of about 6.

Finally, removal of the aprotic solvent catalyst is, as it turns out, a very simple step. Distillation is usually carried out in order to separate the linear products from the cyclics. During this step the volatile aprotic solvent is also removed. Thus, further neutralization or separation equipment for removal of the catalyst is not necessary.

The following examples are given for the purpose of illustrating the invention and should not be read as limiting the scope of the invention.

EXAMPLE 1

A reaction involving methyl-3,3,3-trifluoropropylsiloxane cyclic trimer in acetonitrile and water was effected at room temperature. The reaction is set forth as follows:

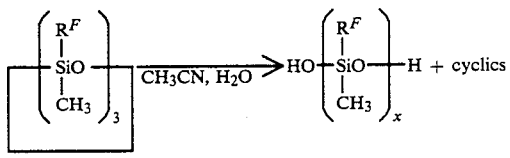

where $R^F$ is $CF_3CH_2CH_2-$ and x is the degree of polymerization. A haze that appears in the composition disappears as the water reacts. The resultant of the reaction was the formation of a silanol terminated fluid having an avg DP of about 6. The reaction initially yielded a trimer diol, however, condensation took place to form a silanol terminated fluid and the cyclics. The amount of cyclics is usually less than 5 percent.

EXAMPLE 2

The reaction described in Example 1 was duplicated using 1,3,5-hexamethylcyclotrisiloxane and using 1,3,5,7-octamethylcyclotetrasiloxane substituted for the methyl-3,3,3-trifluoropropylsiloxane cyclic trimer. In each case no reaction was observed, even after protracted heating to 80° C.

EXAMPLE 3

The reaction described in Example 1 was again duplicated using a mixture of acetone and 350 ppm acetic acid (equivalent to what is found in HPLC grade acetonitrile) substituted for the acetonitrile. Again, no reaction was observed. However, after the addition of 150 ppm of acetonitrile the ring opening reaction was observed after heating at 60° C. for one hour.

EXAMPLE 4

Methyl-3,3,3-trifluoropropylsiloxane cyclic trimer — 150 grams — was dissolved in 152.0 grams of acetonitrile along with 6.1 grams of distilled water. The mixture was agitated at RT until the initial haze — due to water — gradually disappeared. The mixture was then poured into water containing a trace of $NaHCO_3$. The product layer (bottom) was separated and washed several more times with water before being dried over silica gel. The material was filtered and sparged with nitrogen until the FTIR indicated the absence of MeCN. A clear fluid — 133.0 gram, 85.4% yield — was recovered having a viscosity of 675 cps at 25° C. Analysis indicates a water content of 575 ppm and a silanol value of 2.51 wgt %. Reversed phase HPLC — with a solvent blend of 80:20 MeCN:$H_2O$ — indicates cyclics content < 4 wgt %. Linear silanols with a DP of approximately 6 are produced (based on the silanol results).

EXAMPLE 5

The reaction of fluorosilicone cyclic trimer was carried out in mixtures of acetone and acetonitrile plus water while heating for one hour at 60° C. The product was isolated thru a procedure similar to example one except no $NaHCO_3$ was used. The following table summarizes the results. All amounts are in grams unless otherwise indicated.

| Trimer | $H_2O$ | Acetone | Acetonitrile | % SiOH | Visc(cps) | $H_2O$ |
|---|---|---|---|---|---|---|
| 200 | 9.5 | 0 | 200 | 3.70 | 320 | 0.11 |
| 200 | 9.5 | 150 | 50 | 3.4 | 400 | .12 |

-continued

| Trimer | H$_2$O | Acetone | Aceto-nitrile | % SiOH | Visc(cps) | H$_2$O |
|---|---|---|---|---|---|---|
| 200 | 9.5 | 180 | 20 | 3.1 | 296 | 0.10 |
| 200 | 16.5 | 200 | 0.35 | 2.86 | 584 | 0.14 |
| 200 | 17.0 | 200 | 0.03 | 3.53 | 360 | 0.04 |

What is claimed is:

1. A process for producing low molecular weight silanol end-stopped diorganopolysiloxanes containing an average of 3 to 10 diorganosiloxy units and averaging 6 diorganosiloxy units comprising contacting a cyclic trimer of the formula:

[(R$_2$SiO)$_3$] (R$^2$RSiO)$_3$ where R$^2$ is a halogenated monovalent hydrocarbon radical and R is selected from the class consisting of monovalent hydrocarbon radicals and halogenated monovalent hydrocarbon radicals with a mixture comprising an aprotic solvent and water and separating the desired product after the hydrolysis.

2. The process of claim 1, wherein R$^2$ is a C$_{1-8}$ haloalkyl radical and R is selected from the group consisting of C$_{1-8}$ alkyl, C$_{1-8}$ haloalkyl, and C$_{1-8}$ cycloalkyl radicals.

3. The process of claim 1, wherein R$^2$ is a monovalent group of the formula:

R$^1$CH$_2$Ch$_2$— wherein R$^1$ is a perfluoroalkyl radical and R is selected from the group consisting of C$_{1-8}$ alkyl radicals and a monovalent group of the formula:

R$^1$CH$_2$Ch$_2$— wherein R$^1$ is a perfluoroalkyl radical.

4. The process of claim 1, wherein the cyclic trimer is represented by the formula:

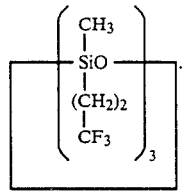

5. The process of claim 1, wherein the aprotic solvent is selected from the class consisting of acetonitrile, dimethylacetimide, dimethylformamide, dimethylsulfoxide, n-methylpyrolidone, and propylene carbonate.

6. The process of claim 1 wherein the aprotic solvent is acetonitrile.

* * * * *

UNITED STATES PATENT OFFICE
CERTIFICATE OF CORRECTION

PATENT NO. : 4,977,290
DATED : December 11, 1990
INVENTOR(S) : Edwin R. Evans and Paul Maitoza It is certified that error appears in the above-identified patent and that said Letters Patent is hereby corrected as shown below:

In the Abstract, the formula should be changed from "$(R^2SiO)_3$" to -- $(R^2RSiO)_3$ --.

In claim 1, line 15, please delete the formula "$[(R_2SiO)_3](R^2RSiO)_3$" and substitute therefor the formula -- $(R^2RSiO)_3$ --.

Signed and Sealed this

Tenth Day of November, 1992

Attest:

DOUGLAS B. COMER

Attesting Officer     Acting Commissioner of Patents and Trademarks